United States Patent
Wolleschensky

(10) Patent No.: US 7,304,280 B2
(45) Date of Patent: Dec. 4, 2007

(54) LASER LINE SCANNING MICROSCOPE AND METHOD OF USE

(75) Inventor: Ralf Wolleschensky, Apolda (DE)

(73) Assignee: Carl Zeiss Jena GmbH, Jena (DE)

( * ) Notice: Subject to any disclaimer, the term of this patent is extended or adjusted under 35 U.S.C. 154(b) by 167 days.

(21) Appl. No.: 10/967,313

(22) Filed: Oct. 19, 2004

(65) Prior Publication Data

US 2006/0011803 A1    Jan. 19, 2006

(30) Foreign Application Priority Data

Jul. 16, 2004    (DE) .................... 10 2004 034 971

(51) Int. Cl.
*G02B 7/04* (2006.01)
(52) U.S. Cl. .................. 250/201.3; 250/208.1
(58) Field of Classification Search ............ 250/201.3, 250/201.4, 201.5, 201.8, 208.1, 234, 235, 250/559.07, 559.06, 559.4; 359/383, 385, 359/368

See application file for complete search history.

(56) References Cited

U.S. PATENT DOCUMENTS

| | | | |
|---|---|---|---|
| 5,420,717 A | 5/1995 | Tabata | |
| 5,932,871 A | 8/1999 | Nakagawa et al. | |
| 6,028,306 A | 2/2000 | Hayashi | |
| 6,167,173 A | 12/2000 | Schoeppe et al. | |
| 6,248,988 B1 | 6/2001 | Krantz | |
| 6,337,474 B1 | 1/2002 | Morizono | |
| 6,449,087 B2 * | 9/2002 | Ogino ................ | 359/383 |

(Continued)

FOREIGN PATENT DOCUMENTS

DE    2360197 A1    6/1975

(Continued)

OTHER PUBLICATIONS

Edited by J. B. Pawley, Handbook of Biological Confocal Microscopy, Second Ed., 1995, Chapter 29, pp. 460-462 "Resonant Galvanometers" (only Fig. 1 appearing on p. 460).

(Continued)

*Primary Examiner*—Que T Le
(74) *Attorney, Agent, or Firm*—Jacobson Holman PLLC

(57) ABSTRACT

In a light raster scanning microscope with illumination arrangement (2) in the form of a line which provides an illumination beam for the illumination of a sample (23) in the form of points or point groups, a scanning arrangement (3, 4) which guides the illumination beam in the form of points or point groups over the sample in a manner so as to scan, a spot detector arrangement (5) which images, via the scanning arrangement (3, 4), the illuminated point or point group spot of the sample (23) by means of at least one confocal aperture (26) on at least one detector unit (28), and a control unit which controls the scanning arrangement (3, 4) and reads out the spot detector arrangement (5), it is provided that, in addition, a wide-field illumination source (29, 34) is provided which illuminates the sample (23) and that the control unit controls the scanning arrangement (3, 4) during the operation of the wide-field illumination source (29, 34) and reads out the spot detector arrangement (5) in such a manner that an image of the sample (23) subject to wide-field illumination is obtained.

14 Claims, 3 Drawing Sheets

U.S. PATENT DOCUMENTS

| | | | |
|---|---|---|---|
| 6,486,458 | B1 | 11/2002 | Schoeppe et al. |
| 6,563,632 | B1 | 5/2003 | Schoeppe et al. |
| 6,631,226 | B1 | 10/2003 | Schoeppe |
| 6,831,780 | B2 | 12/2004 | Knebel |
| 6,888,148 | B2 | 5/2005 | Wolleschensky et al. |
| 2003/0142292 | A1 | 7/2003 | Wolleschensky et al. |

FOREIGN PATENT DOCUMENTS

| | | |
|---|---|---|
| DE | 19702753 A1 | 7/1998 |
| DE | 10257237 A1 | 6/2003 |
| EP | 1128200 A2 | 11/2000 |
| WO | WO 8807695 | 10/1988 |

OTHER PUBLICATIONS

M.-A. Abdul-Karim et al., "Automated tracing and change analysis of angiogenic vasculature from in vivo multiphoton confocal image time series," Microvascular Research 66 (2003), pp. 113-125.

F. Umenishi et al., "cAMP Regulated Membrane Diffusion of a Green Fluorescent Protein-Aquaporin 2 Chimera," Biophysical Journal, vol. 78, Feb. 2000, pp. 1024-1035.

H.L. Zhang et al., "Neurotrophin-Induced Transport of a β-Actin mRNP Complex Increases β-Actin Levels and Stimulates Growth Cone Motility," Neuron, vol. 31, Aug. 2, 2001, pp. 261-275.

M. A. Petersen et al., "Diverse Microglial Motility Behaviors During Clearance of Dead Cells in Hippocampal Slices," Motility of Phagocylic Microglia, 2004, pp. 195-206.

S. Bertera et al., "Body window-enabled in vivo multicolor imaging of transplanted mouse islets expressing an insulin-Timer fusion protein," BioTechniques, vol. 35, No. 4 (2003), pp. 718-722.

G. Brum et al., "Fast imaging in two dimensions resolves extensive sources of $Ca^{2+}$ sparks in frog skeletal muscle," Journal of Physiology (2000), 528.3, pp. 419-433.

H. Schmidt et al., "Mutational analysis of dendritic $Ca^{2+}$ kinetics in rodent Purkinje cells: role of parvalbumin and calbindin $D_{28k}$," Journal of Physiology (2003), 551.1, pp. 13-32.

* cited by examiner

LASER LINE SCANNING MICROSCOPE AND METHOD OF USE

BACKGROUND OF THE INVENTION

1. Field of the Invention

The invention relates to a confocal laser scanning microscope with a spot illumination arrangement which provides an illumination beam for the illumination of a sample by points or point groups, a scanning arrangement which guides the illumination beam by points or point groups over the sample in a manner so as to scan, a spot detector arrangement which images, via the scanning arrangement, the point or point group spot of the sample by means of at least one confocal aperture on at least one detector unit, and a control unit which controls the scanning arrangement and reads out the spot detector arrangement.

The invention further relates to a process for laser scanning microscopy, wherein an image of a sample is generated by scanning and confocal imaging of a point or point group spot and means are provided for the illumination of the scanned point or point group spot.

2. Related Art

Confocal laser scanning microscopes of the type stated initially are known in the state of the art, by way of example let reference be made to DE 197 02 753 A1. Recently microscope accessories, in particular confocally imaging laser scanning microscopes, have been used increasingly for spectroscopic exposure technologies. In this way it is possible to measure the spectroscopic properties of a selected sample area without damage or contact. The confocal optical microscope makes possible in this way the selective detection of optical signals which are generated within a diffraction-limited confocal volume whose size lies in the micrometer range. Laser scanning microscopes with sampling laser beams and/or sample feed units can produce with a high spatial resolution two-dimensional or three-dimensional representations of the sample examined. Due to this property, confocal laser scanning microscopy has achieved success for fluorescing samples in the biomedical field, nearly as the standard.

Beyond said fluorescence measurement, said DE 197 02 753 A1 also provides for carrying out a transmission measurement on the sample. For this, a detector can be activated which, relative to the direction of illumination of the scanned laser radiation, lies below the sample and which picks up the transmitted percentage of the radiation beamed in the form of a point via the scanner. Thereby a so-called "transmitted light scan" is realized. The optical linking of the detector lying below the sample presents certain difficulties, in particular since one customarily also provides an optical viewing device for an observer on the microscope part of the laser scanning microscope. This has as a consequence the fact that a change-over between the illumination for the normal microscope and the separate detector for the transmitted light scan is required.

SUMMARY OF THE INVENTION

The objective of the invention is to extend a microscope of the type stated initially so that transmission measurements on the sample can be performed without increased effort.

This objective is realized according to the invention with a laser scanning microscope of the type stated initially in which, in addition, a wide-field illumination source is provided which illuminates the sample and in which the control unit controls the scanning arrangement during the operation of the wide-field illumination source and reads out the spot detector arrangement in such a manner that an image of the sample (23) subject to wide-field illumination is obtained.

The invention is furthermore realized with a process for laser scanning microscopy of the type stated initially in which the sample is illuminated with wide-field illumination and is imaged by scanning the point or point group spot.

The invention therefore uses for the first time a wide-field illumination in combination with scanned detection. With this surprisingly simple measure a separate detector can be omitted. At the same time one is achieves an abundance of advantages.

For wide-field illumination, radiation sources can be used which are present in any case on the laser scanning microscope for normal optical observation. A change-over mechanism is no longer needed. A simplification overall, from the standpoint of construction, therefore results. Preferably the wide-field illumination radiation source will realize a transmitted light illumination of the sample. Alternatively, and in addition, a wide-field incident-light illumination is naturally also possible in order, for example, to carry out epifluorescence measurements or reflection measurements. Also both modes (incident light and transmitted light) can be realized simultaneously.

The capability of the confocal detector arrangement allows for the first time a highly resolved transmission measurement.

Through the use of the wide-field illumination radiation sources, usually present in any case, which are usually very broad-band compared to the excitation illumination sources provided for scanning, a white light transmitted light mode can be realized which, due to the requirements of confocal imaging in customary laser-scanning microscopes, was not possible in this manner or only at enormous expenditure on the light-source side. The same applies analogously with regard to wide-field incident-light fluorescence excitation.

Through the sampling with the scanned detectors of the sample subject to wide-field illumination, a spectral the detector arrangement's spectral analysis capability present in a laser-scanning microscope can also be exploited in transmission mode, which leads to an improved sample characterization. An extension is thus preferred in which the spot detector arrangement comprises several spectral channels.

The wide-field illumination can be operated independently of the scanned illumination in the form of a spot. Naturally, the control unit can also introduce a simultaneous mode in which the sample is then analyzed simultaneously in transmission as well as in the customary fluorescence mode.

For example, the control unit can suitably read out several channels so that fluorescence information about the sample arrives in several spectral channels, transmission information in other spectral channels. A suitable combination of this information, e.g. in a superimposed image, gives a sample analysis superior to customary systems. It is thus preferred that the control unit controls the spot illumination arrangement and the wide-field illumination source simultaneously during operation and reads out the spectral channels of the spot detector arrangement suitably.

A further advantage of the approach according to the invention lies in the fact that a transmitted light scan is also possible at several points, which customary, separate detectors disposed under the sample do not allow due to the lack of suitable spatial resolution. The use of a multi-point or point group scanner in transmitted light mode now opened up by the invention reduces any problems due to temporal fluctuations of the wide-field illumination since it can be compensated by suitable extension of the integration time in multi-point or point group systems. It is thus preferred that the wide-field illumination and the scanned point or point group illumination be performed simultaneously. Point group is understood to mean any arrangement of several points, in particular in the form of a line, which the laser scanning microscope confocally illuminates and images. Through this approach, further advantageously lower sample loads or shorter measuring times are realized, which in the state of the art were not possible in this manner. It is thus particularly preferred that the spot detector arrangement realizes a confocal point group imaging, for example, with at least one Nipkow disk and at least one matrix detector.

Here reference is made to multi-point or Nipkow arrangements in U.S. Pat. No. 6,028,306, WO 88 07695, or DE 2360197 A1, which are incorporated into the disclosure.

Also included are resonance scanner arrangements, as are described in Pawley, Handbook of Biological Confocal Microscopy, Plenum Press 1994, page 461 ff.

Also the spot detector arrangement can also use a confocal slit diaphragm with a line detector if a line serves as a point group.

The use of wide-field illumination finally opens completely new contrasting processes for transmitted light measurement. Now all the contrasting processes are possible, as they are known in the state of the art for customary optical light microscopes. In order to realize this it is to be preferred that the wide-field illumination source comprises a condensing lens into which contrasting means can be connected. For example, dark-field illumination can be realized by disposing a suitable annular disk in the capacitor.

Still other contrasting methods are, however, also conceivable if the scanning arrangement comprises a scanning objective into whose pupil plane suitable contrasting means can be connected. In combination with the linking of contrasting means to the condensing lens, not only dark-field contrast but rather also phase contrast, VAREL contrast, polarization contrast, or differential interference contrast are possible.

BRIEF DESCRIPTION OF THE DRAWINGS

The invention is explained in more detail, by way of example, in the following, with reference to the drawings. Shown in the drawings are.

DETAILED DESCRIPTION OF THE PREFERRED EMBODIMENTS

Figure 1:
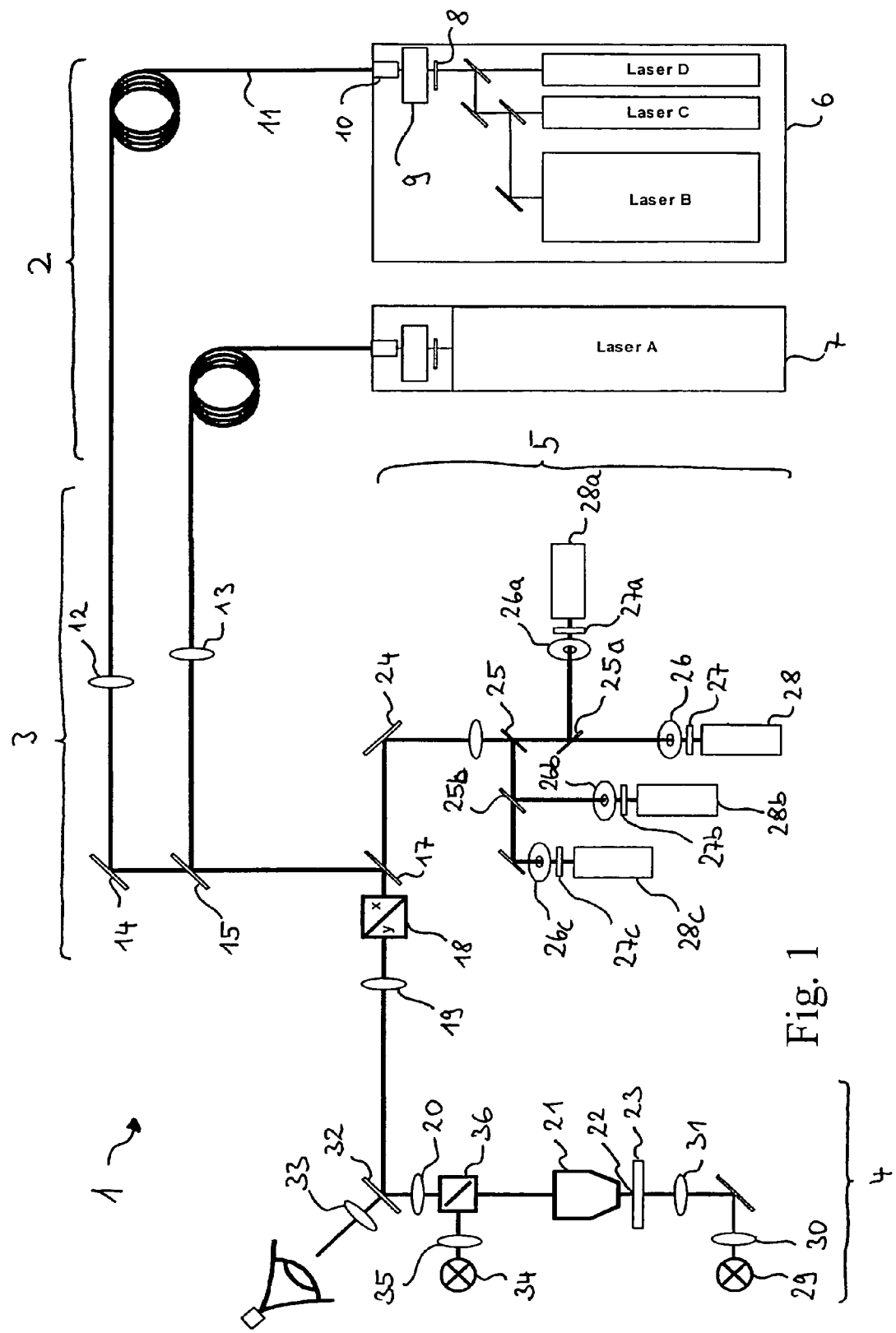
FIG. 1 a schematic representation of a point-scanning laser scanning microscope, FIG. 2 a schematic representation of a laser scanning microscope laser scanning microscope scanning point groups, FIG. 3 a schematic representation of the laser scanning microscope of FIG. 2 in a first section plane, FIG. 4 a principal beam splitter of the laser scanning microscope of FIG. 2.

FIG. 1 shows schematically a laser scanning microscope 1 which is assembled essentially from five components: a radiation source module 2 which generates the excitation radiation for laser scanning microscopy, a scanning module 3 which conditions, and suitably deflects, the excitation radiation for scanning over the sample, a microscope module 4 which directs the scanning radiation provided by the scanning module in a microscopic beam path onto a sample, and a detector module 5 which receives and detects optical radiation from the sample. The detector module 5 can be implemented in this case, as is represented in FIG. 1, to have multiple spectral channels.

The radiation source module 2 generates illumination radiation which is suitable for laser scanning microscopy, therefore in particular radiation which can resolve fluorescence. Depending on the application, the radiation source module comprises several radiation sources for this purpose. In a form of embodiment represented two lasers 6 and 7 are provided in the radiation source module to each after each of which a light valve 8 as well as an attenuator 9 are connected and which couple their radiation via a coupling point 10 into a light guide fiber 11. The light valve 8 acts as a beam deflector with which switching off of a beam can be caused without the operation of the lasers in the laser unit 6 or 7 themselves having to be switched off. The light valve 8 is, for example, formed as AOTF which deflects the laser beam, before coupling into the light guide fiber 11, in the direction of a light trap not represented.

In the exemplary representation of FIG. 1 the laser unit 6 comprises three lasers B, C, and D, while on the other hand the laser unit 7 contains only one laser A. The representation in FIGS. 6 and 7 is therefore exemplary for a combination of individual and multi-wavelength lasers which are coupled individually, or also jointly, to one or more fibers. Also the coupling can be done simultaneously via several fibers whose radiation is mixed by color combiners, later after running through adaptation optics. It is thus possible to use the most varied wave lengths or ranges for the excitation radiation.

The radiation coupled into the light guide fiber 11 is synthesized via beam synthesis mirrors 14, 15 by means of displaceable collimation optics 12 and 13.

The collimators 12, 13 provide that the radiation supplied by the radiation source module 2 to the scanning module 3 is collimated into an infinite beam path. This is done in each case advantageously with a single lens which, by displacement along the optical axis under control (of a not represented) central drive unit, has a focusing function in that the distance between collimator 12, 13 and the respective end of the light guide fiber can be changed.

This illumination beam serves as excitation radiation and is conducted via a principal color splitter 17 to a scanner 18. On the principal color splitter it is later received, here let it merely be mentioned that it has the function of separating sample radiation returning from the microscope module 4 from the excitation radiation.

The scanner 18 redirects the beam diaxially, after which it is bundled by a scanning objective 19, as well as a tubular lens 20 and an objective 21, into a focus 22 which lies in a preparation or in a sample 23. The optical imaging is done in this process so that the sample 23 is illuminated at a focal point with excitation radiation.

Fluorescence radiation excited in this manner in the focus 22 in the form of a line arrives via the objective 21, the tubular lens 20, and the scanning objective 19 back at the scanner 18 so that in the rear direction after the scanner 19 there is once more an inactive beam. One thus also speaks of the scanner 19 de-scanning the fluorescence radiation.

The principal color splitter 17 lets the fluorescence radiation lying in wavelength ranges other than the excitation radiation pass so that it can be reversed and then analyzed via a reversing mirror 24 in the detector module 5. The detector module 5 comprises in the form of embodiment of FIG. 1 four spectral channels, that is, the fluorescence radiation coming from the reversing mirror 24 is split by means of auxiliary color splitters 25, 25*a*, 25*b*, 25*c* into four spectral channels.

Each spectral channel comprises a confocal pinhole aperture 26 which realizes a confocal imaging with respect to the sample 23 and whose magnitude determines the depth resolution with which the resolution can be detected. The geometry of the aperture 26 thus determines the sectional plane within the (thick) preparation from which radiation is detected.

The aperture 28 is still disposed behind a block filter 27 which blocks undesired excitation radiation reaching the detector module 5. The radiation separated off in this manner, stemming from a certain depth section, and expanded in the form of a row is then analyzed by a suitable detector 28. The additional spectral detection channels are also assembled analogously to the described first color channel, said additional spectral detection channels also including a pinhole aperture 26*a* or 26*b*, 26*c*, a block filter 27*a* or 27*b*, 27*c*, and a detector 28*a*, or 28*b*, 28*c*.

Along with the confocal sampling of a sample area illuminated with a focal point or focal line, the laser scanning microscope 1 of FIG. 1, in the represented optional mode of construction relating to this, also makes possible another mode of measurement. For this, a halogen lamp 29 is provided whose radiation is directed onto the sample 23 in wide-field illumination contrary to the direction of viewing of the scanning optics 19 via lamp optics 30 and a condensing lens 31. Portions transmitted by this illumination are also sampled by the objective 21, the tubular lens 20, the scanning objective 19, and the scanner 18 in the scanning process and analyzed spectrally by means of the principal color splitter 17 and the secondary color splitter in the detector module 5. The detection via the scanner 18 causes the spatial resolution in the form of the sampling of the sample and at the same time wide-field illumination via the halogen lamp 29 is possible.

The same concept can also be used for the evaluation of back-reflected radiation and epifluorescence in which, via a mercury vapor lamp 34 with lamp optics 35 on a beam splitter 36, illumination radiation is coupled into the tube of the microscope module 4. This radiation then arrives via the objective 21 at the sample 23. Also here the illumination is done without the cooperation of the scanner 18. The detection is done, on the contrary, once again via the scanning optics 19 and the scanner 18 in the detector module 5. The detector module 5 thus has, for this extension, a double function. On the one hand it serves as detector for excitation radiation beamed in scanned. On the other hand, the detector module 5 acts as a spatially resolving detector if radiation which is not structured further is beamed onto the sample, namely either as wide-field illumination from below or via the objective 21. However, the scanner 18 also has a double action since it achieves the spatial resolution by sampling, in the form of points, of the sample not only with beamed-in excitation radiation in the form of points but rather also with wide-field illumination.

Through this approach, detectors not scanned in the transmission or incident light mode on the microscope module 4 can be spared.

Moreover, the laser scanning microscope 1 of FIG. 1 makes possible a combination mode in which beamed-in excitation radiation in the form of points or point groups is directed from the radiation source module 2, as well as wide-field illumination from the halogen lamp 29 or the mercury vapor lamp 34, onto the sample 23 and, by means of the scanner 18 and the detector module 5, a corresponding sampling in the form of points or point groups of the sample multiply radiated in this manner is achieved. By suitable choice of the secondary color splitter 25 to 25*c* the classical transmission or reflection microscopy can be combined with laser fluorescence measurement. The image data thus obtained by sampling by means of the evaluation of the signals of the detectors 28 to 28*c* can then be evaluated or represented independently or superimposed.

Figure 2:
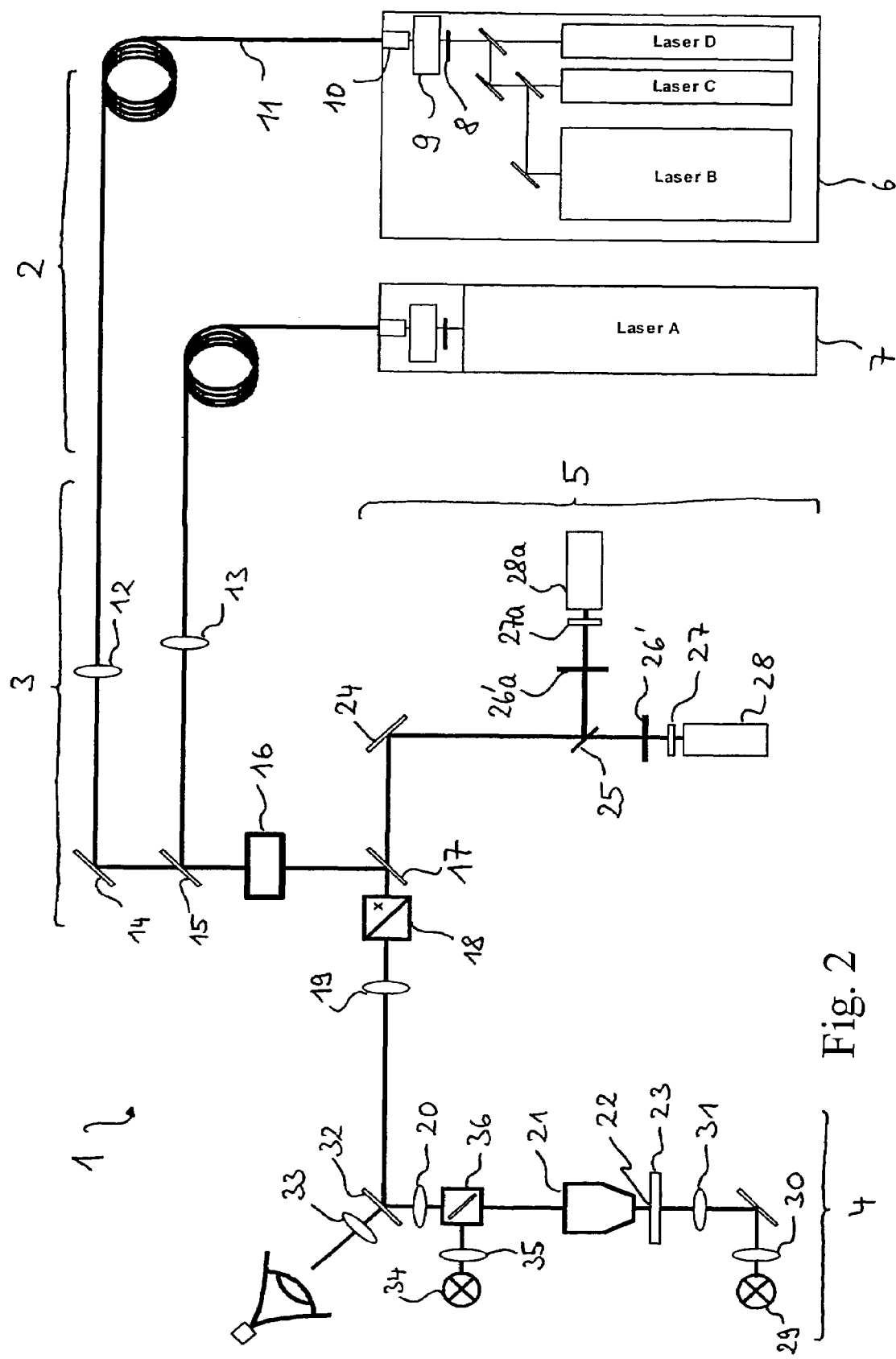

The mode of construction of FIG. 1 is, in particular with regard to the detector module 5, merely to be understood as an example. FIG. 2 showed an alternative mode of construction in which, instead of a focus 22 in the form of point, a confocal imaging in the form of lines is used. For this, instead of pinhole apertures 26, slit diaphragms 26' are provided in the detector module 5, which, by way of example, is then equipped with two spectral channels.

This partially confocal imaging in the form of a slit naturally also needs a corresponding illumination of the sample 23 by the laser radiation module 3 with a focal line. A beam-forming unit 16 is thus disposed behind the beam-combining mirrors 14 and 15 in addition in the mode of construction of FIG. 2, said beam-forming unit producing, from the rotationally symmetric, Gaussian-shaped laser beam supplied by the lasers, a beam in the form of a row which is no longer rotationally symmetric but rather is suitable in cross-section for the generation of a rectangularly illuminated field. The scanner 18 thus redirects an illumination beam to be designated as in the form of a row as excitation radiation over the sample 23. With sufficient length of the focal line the scanner 18 can then, as FIG. 2 shows, be restricted to a single-axis redirection.

The use of a confocal slit aperture in the detector module 5 is only exemplary. In principle arbitrary multi-point arrangements, such as point cloud or Nipkow disk concepts, can be used. However, it is essential that the detector 28 is then spatially resolving so that a parallel recording of several sample points is done in one pass of the scanner.

Through this concept the non-descanned detectors on the microscope module 4 previously required in the state of the art are omitted. Furthermore, by the confocal detection, a high spatial resolution can be achieved, which otherwise would be achievable in the case of non-descanned detection only with complicated matrix sensors. Moreover, temporal fluctuations of the wide-field illumination beamed in, e.g. of the halogen lamp 29 or the mercury vapor lamp 34 among others, can be switched off by a suitable integration in the spatially resolving detector 28, 28*a*.

For this mode of operation the laser scanning microscope 1, the principal color splitter 17, as well as the secondary color splitter 25, is naturally appropriately set. This also makes it possible to perform both modes of operation, i.e. wide-field illumination from below and illumination through the objective 21, simultaneously if the color splitters are equipped a suitable dichroites.

Also arbitrary combinations with scanned illumination from the radiation source module 2 are possible. A correspondingly superimposed graphic representation of the evaluated signals then offers far superior image information relative to customary concepts.

The combination of a confocal multi-point imaging, e.g., a line scanner, with a spectral multi-channel detection makes possible a highly parallel data acquisition. An image acquisition rate of over 200 images per second can be achieved and there is a real-time capability previously not realized for laser scanning microscopes. Alternatively, the laser scanning microscope 1 also makes possible a highly sensitive detection of particularly weak signal intensities. Compared with a confocal single-point laser scanning microscope, for the same image acquisition time, the same surface imaged in the sample, the same field of view, and the same laser power per pixel, a signal/noise ratio is realized which is improved by a factor of $\sqrt{n}$, where n denotes the number of multi-point imagings. For one detector row a value of 500 to 2,000 is typical.

The radiation source module 2 of the laser scanning microscope 1 meets the prerequisite necessary for this, namely that the multi-point illumination, e.g. the illumination row which, e.g. is provided by the radiation-forming unit 16, has power n times that of the laser focus of a comparable confocal single-point scanner.

Alternatively, the sample load, i.e. the amount of radiation to which the sample is exposed and which can lead to bleaching of the sample, can, in comparison to the confocal single-point scanner with the same image acquisition time and the same signal/noise ratio, be reduced by a factor n if the radiation power previously used in a confocal single-point scanner is distributed only onto several points, e.g. the row.

The multi-point sampling laser scanning microscope therefore makes it possible in comparison to the confocal single-point scanners to image weak-intensity signals of sensitive sample substances with the same surface signal/noise ratio and the same sample load faster by a factor of n, with the same image acquisition time, with a signal/noise ratio improved by a factor of $\sqrt{n}$, or with the same image acquisition time, with the same signal/noise ratio, and a sample load lower by a factor of n.

Figure 3:
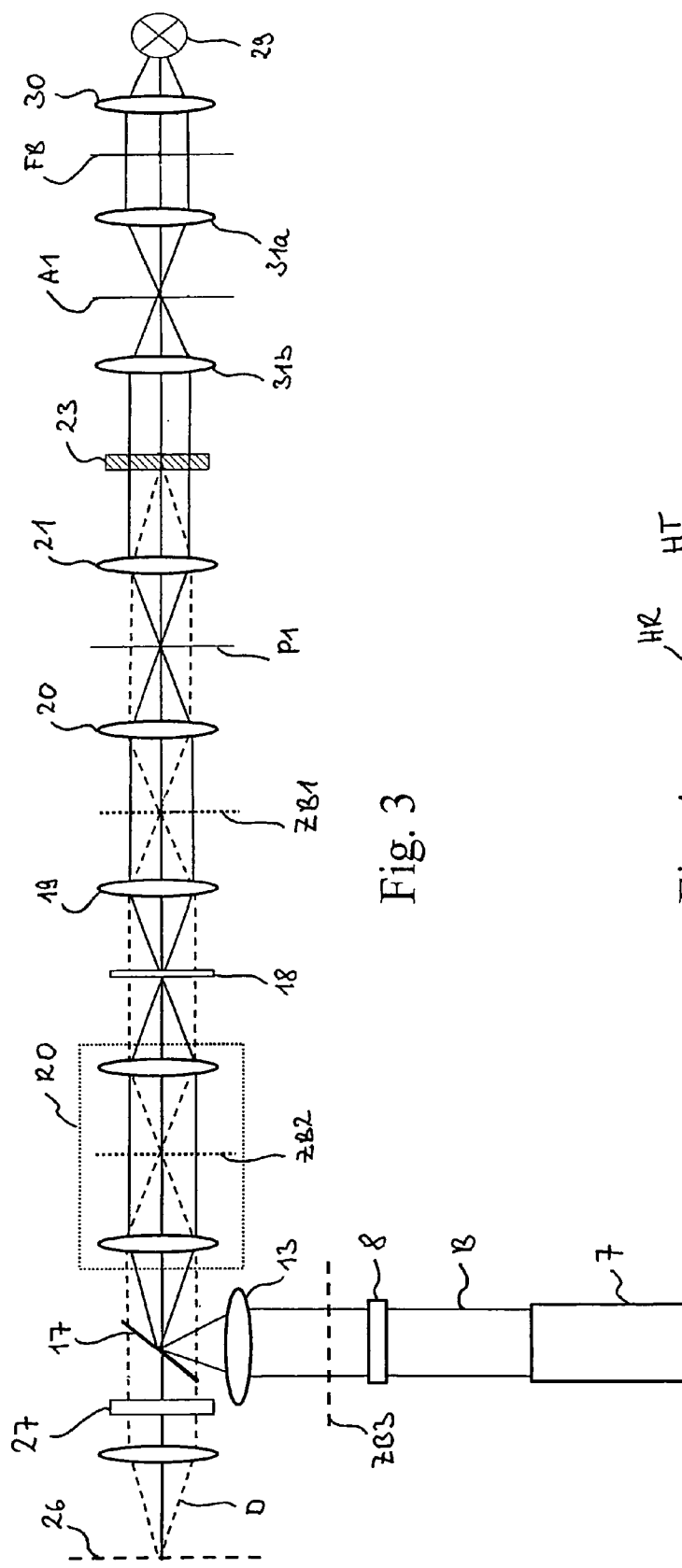

FIG. 3 shows schematically an exemplary radiation beam path for the laser scanning microscope 1 of FIG. 1 or 2 in the mode of construction with a line scanner. The point group is here therefore realized as a row. Accordingly, the illuminated spot is a line. As in FIGS. 1 and 2, components already appearing there are denoted with the same reference numbers, on account of which reference in made at least partially to FIGS. 1 and 2 with regard to the description.

In FIG. 3 the illumination beam path B is illustrated with solid lines, while on the contrary the detection beam path D is represented by a dotted line. FIG. 3 shows that the sample 23 is illuminated in two ways. On the one hand, for the two optics 31a, 31b drawn in FIG. 3, there is wide-field illumination via the halogen lamp 29, the lamp optics 30, and the condensing lens 31. On the other hand, the laser 7 causes a linear illumination, on account of which the representation in FIG. 3 has no focus in the sample in the sectional direction shown.

Figure 4:
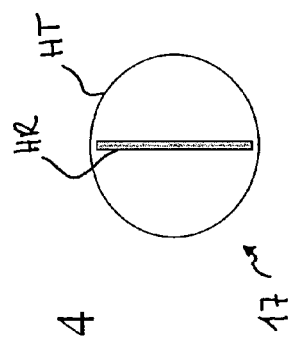

The scanner 18 redirects a line over the sample 23 and images it confocally onto a confocal aperture 26 assigned to the spot image, said aperture being formed as a slit diaphragm due to the linear spot. In the sample 23 the coherence of the excitation radiation incident in the form of a line is disrupted by the fluorescence excitation since fluorescence is an incoherent interaction. The dimension of the dye molecules lies below the optical resolution of the microscope. Each dye molecule radiates as a point radiator independently of the other sample locations and fills the entire objective pupil. The result is the detection beam path drawn in FIG. 3 as a dotted line. The illumination in the form of a spot which can be realized in this manner as a focal line is separated via the principal color splitter 17 from the detection beam path D. This principal color splitter is implemented as a strip mirror according to DE 10257237 in the present form of embodiment. It is shown in plan view in FIG. 4. Such a strip mirror, which comprises a highly reflective part HR and a highly transmitting part HT, acts as a spectrally independent principal splitter. It lies, as can be seen, in a pupil plane of the scanner arrangement in which focusing is in the form of a line (in the case of a single-point detector) reflected in the sample plane, i.e. coherent illumination radiation. Incoherent signal radiation to be detected, on the contrary, fills the entire pupil plane and is essentially transmitted by the highly reflecting part HT. In the sense of the invention, the term "color splitter" is therefore also to be understood to mean a splitter acting non-spectrally.

For wide-field illumination a field aperture is provided between the lamp optics 30 and the condensing lens 31a, 31b in order to be able to adjust the illuminated area. Furthermore, an aperture stop A1 can be connected into the condensing lens 31a, 31b. It lies in conjugated position relative to the pupil planes of the laser scanning microscope. These pupil planes are the pupil plane P1, the plane in which the scanner 18 lies, and the plane in which the principal color splitter 17 is disposed. As aperture stop A1, as well as in the pupil plane P1, different optical elements can be used in order to use known contrasting methods from classical microscopy, such as, for example, dark field, phase contrast, VAREL contrast, or differential interference contrast. Suitable aperture stops A1, or elements to be introduced in the pupil plane P1, are, for example, explained in the publication "Microscopy from the very beginning", Carl Zeiss Mikroskopie, D-07740 Jena, 1997, Pages 18-23. The contents of the disclosure of the company publication are not explicitly incorporated here relating to this. For such contrasting interventions, naturally not only the pupil plane P1 is suitable. Also other pupil planes are also fit for this. For example, the intervention can also be done in the vicinity of the principal color splitter 17 or by means of relay optics after the secondary color splitter 25 (or several) spectral channels of the detector beam path.

The beam path of FIG. 3 comprises, in addition to the elements already described with the aid of FIGS. 1 and 2, relay optics RO which provide, in addition to the intermediate image plane ZB1 between the scanning optics 10 and tube lens 20, an additional intermediate image plane ZB2 for the illumination beam path. A third intermediate image plane ZB3 of the intermediate image plane is located in front of the principal color splitter 17 so that a pupil plane is created for the color splitter. If one wants to keep the design compact, the relay optics RO can also be omitted.

The described invention represents a significant expansion of the possibilities for application of fast confocal laser scanning microscopes. The significance of such a further development can be with the aid of the standard literature in cellular biology and the fast cellular and subcellular processes described there and the methods of study with a plurality of dyes.

See, for example,

B. Alberts et al. (2002): Molecular Biology of the Cell; Garland Science.

G. Karp (2002): Cell and Molecular Biology: Concepts and Experiments; Wiley Text Books.

R. Yuste et al. (2000): Imaging neurons—a laboratory Manual; Cold Spring Harbor Laboratory Press, New York.

R. P. Haugland (2003): Handbook of fluorescent Probes and research Products, 10th Edition; Molecular Probes Inc. and Molecular Probes Europe BV.

The invention has, in particular, great importance for the following processes:

Development of Organisms

The described invention is, among other things, suitable for the study of developmental processes which are distinguished, above all, by dynamic processes in the tenth of a second to the hour range. Exemplary applications at the level of united cell structures and entire organisms are, for example, described here:

Adbul-Karim, M. A. et al. have described in 2003 in Microvasc. Res. 66: 113-125 a long-term analysis of blood vessel changes in living animals, where fluorescence promoters were recorded at intervals over several days. The 3D-data sets were evaluated with adaptive algorithms in order to represent the trajectories of motion schematically.

Soll, D. R. et al. have described in 2003 in Scientific World Journ. 3: 827-841 a software-based analysis of motion of microscopic data in nuclei and pseudopodiae of living cells in all 3 spatial dimensions.

Grossmann, R. et al. have described in 2002 in Glia 37: 229-240 a 3D-analysis of the motions of microglial cells in rats, where the data were gathered over up to 10 hours. Simultaneously, very fast reactions of the glia also occurred after traumatic injury so that a high data rate and corresponding data volume arises.

That relates, in particular, to the following points of emphasis:

Analysis of living cells in a 3D-environment whose neighboring cells react sensitively to laser illumination and which must be protected from the illumination of the 3D-ROI, Analysis of living cells in a 3D-environment with markings which are intended to be selectively bleached by laser illumination in 3D, for example, FRET experiments, Analysis of living cells in a 3D-environment which are intended to be selectively bleached by laser illumination in 3D and are also intended to be observed simultaneously outside of the ROI, for example FRAP and FLIP experiments in 3D, Selective analysis of living cells in a 3D environment with markings and drugs which exhibit the manipulation-related changes by laser illumination, for example, activation of transmitters in 3D, Selective analysis of living cells in a 3D environment with markings which exhibit the manipulation-related color changes by laser illumination, for example, paGFP, Kaede, Selective analysis of living cells in a 3D environment with very weak markings which, for example, require an optimal balance of confocality against detection sensitivity, Living cells in a 3D united tissue structure with varying multiple markings, for example, CFP, GFP, YFP, DsRed, HcRed, among others, Living cells in a 3D united tissue structure with markings which exhibit color changes related to function, for example, $Ca^+$ markers, Living cells in a 3D united tissue structure with markings which exhibit color changes related to development, for example, transgenic animals with GFP, Living cells in a 3D united tissue structure with markings which exhibit manipulation-related color changes by laser illumination, for example, paGFP, Kaede Living cells in a 3D united tissue structure with very weak markings which require a restriction of confocality to promote detection sensitivity, The last point in combination with the preceding ones.

Transport Processes in Cells

The described invention is excellently suited to the study of internal cellular transport processes since therein quite small motile structures, e.g. proteins, must be represented at high speed (usually in the range of hundredths of a second). In order to record the dynamics of complex transport processes, applications such as FRAP with ROI bleaches are also often used. Examples of such studies are, for example, described here Umenishi, F. et al. have described in 2000 in Bipohys. J. 78: 1024-1035 an analysis of the spatial motility of aquaporin in GFP-transfected culture cells. For this, in the cell membrane points were selectively locally bleached and the diffusion of the fluorescence in their vicinity was analyzed.

Gimpl, G. et al. have described in 2002 in Prog. in Brain Res. 139: 43-55 experiments with ROI bleaches and fluorescence imaging for the analysis of mobility and distribution of GFP marked oxytocin receptors in fibroblasts. Therein high demands are placed on the spatial positioning and resolution as well as the direct temporal sequence of bleaching and imaging.

Zhang, et al. have described in 2001 in Neuron 31: 261-275 live cell imaging of GFP-transfected nerve cells, where the motion of granuli was analyzed by combined bleaching and fluorescence imaging. Therein the dynamics of the nerve cells makes great demands on the speed of the imaging.

Interactions of Molecules

The described invention is, in particular, suited to the representation of molecular and other subcellular interactions. Therein very small structures must be represented with high speed (in the range around one hundredth of a second). In order to resolve the molecule's spatial position necessary for the interaction, indirect techniques such as, for example, FRET with ROI bleaches are to be used. Exemplary applications are, for example, described here:

Petersen, M. A. and Dailey, M. E. have described in 2004 in Glia 46: 195-206 a two-channel recording of living hippocampus cultures of rats, where the two channels are plotted spatially in 3D and over a rather long time for the markers lectin and sytox, Yamamoto, N. et al. have described in 2002 in Clin. Exp. Metastasis 20: 663-638 a two-color imaging of human firbrosarcoma cells, where green and red fluorescent protein (GFP and RFP) were observed simultaneously in real-time, Bertera, S. et al. have described in 2003 in Biotechniques 35: 718-722 a multi-coloring of transgenic mice marked with timer reporter protein which changes its color after synthesis from green to red. The image acquisition is done as a fast series 3-dimensionally in the tissue in the living animal.

Signal Transmission between Cells

The described invention is outstandingly well-suited to the study of usually extremely fast signal transmission processes. These usually neurophysiological processes place the highest demands on the temporal resolution since the activities mediated by ions play out in the range of hundredths to less than thousands of a second. Exemplary applications of studies in muscle or nerve systems are, for example, described here:

Brum G. et al. have described in 2000 in J. Physiol. 528: 419-433 the localization of fast $Ca^+$ activities of the frog after stimulation with caffeine as a transmitter. The localization and micrometer-precise resolution succeeded only through the use of a fast confocal microscope.

Schmidt H. et al. have described in 2003 in J. Physiol. 551: 13-32 an analysis of $Ca^+$ ions in nerve cell processes of transgenic mice. The study of fast $Ca^+$ transients in mice with altered $Ca^+$-binding proteins could only be carried out with highly resolving confocal microscopy since even the localization of the Ca$^+$-activity within the nerve cell and its precise temporal kinetics plays an important role.

The invention claimed is:

1. A laser line scanning microscope comprising:
spot illumination means for providing an illumination beam for the illumination of a sample in the form of a line,
a wide-field illumination source for illuminating the sample with wide-field illumination,
scanning means for guiding the illumination beam in the form of a line over the sample so as to scan the sample, and for achieving spatial resolution by sampling of the sample both with illumination in the form of a line from the spot illumination means and with wide-field illumination from the wide-field illumination source,
spot detector means including at least two spectral channels and a detector unit associated with each of the spectral channels for imaging, via the scanning means, the sample area illuminated by the spot illumination means and by the wide-field illumination source onto the detector units of different spectral channels, and
control means for controlling the scanning means during the operation of the wide-field illumination source and for controlling the spot detector means for reading out the spectral channels of the detector means for obtaining an image of the sample subject to wide-field illumination.

2. Laser line scanning microscope according to claim 1, wherein the wide-field illumination source realizes one of transmitted light illumination for transmission measurement and incident light illumination of the sample for fluorescence excitation.

3. Laser line scanning microscope according to claim 1, wherein the control unit controls the spot illumination means and the wide-field illumination source simultaneously during operation.

4. Laser line scanning microscope according to claim 1, wherein the spot detector means comprises at least one Nipkow disk and at least one matrix detector.

5. Laser line scanning microscope according to claim 1, wherein the spot detector means comprises at least one slit diaphragm and at least one row detector.

6. Laser line scanning microscope according to claim 1, wherein the wide-field illumination source comprises a condensing lens configured for connection with means for adjusting the illuminated area.

7. Laser line scanning microscope according to claim 1, wherein the scanning means includes a scanning objective which directs the illumination beam in the form of a line to which at least one pupil plane P1 is assigned, the scanning objective being configured for connection into the pupil plane of means for adjusting the illuminated area.

8. Process for laser line scanning microscopy using the laser line scanning microscope according to claim 1, comprising the steps of:
(a) illuminating a sample with an illumination beam in the form of a line,
(b) subjecting the sample to wide field illumination, and
(c) generating an image of the sample by scanning and confocal imaging of the line of the sample illuminated by the illumination beam and the area of the sample illuminated by the wide-field illumination.

9. Process according to claim 8, wherein in step (b), the sample is illuminated by transmitted light with the wide-field illumination.

10. Process according to claim 8, wherein in step (c), the confocal imaging is performed with spectral resolution.

11. Process according to claim 10, wherein the wide-field illumination of step (b) and the illumination of step (a) are performed simultaneously.

12. Process according to claim 8, wherein in the confocal imaging of step (c), at least one Nipkow disk is used in combination with at least one matrix detector.

13. Process according to claim 8, wherein in the confocal imaging of step (c), at least one slit diaphragm is used in combination with at least one row detector.

14. Process according to claim 8, further comprising the step of using one of phase contrast, dark-field contrast, VAREL contrast, polarization contrast, and differential interference contrast, as a contrasting method.

* * * * *